(12) United States Patent
Andersen

(10) Patent No.: US 10,783,223 B2
(45) Date of Patent: Sep. 22, 2020

(54) HYBRID SIGNAL PROCESSING CIRCUIT FOR IMPLANTABLE MEDICAL DEVICES AND METHODS

(71) Applicant: PACESETTER, INC., Sylmar, CA (US)

(72) Inventor: Dean Andersen, San Jose, CA (US)

(73) Assignee: PACESETTER, INC., Sylmar, CA (US)

( * ) Notice: Subject to any disclaimer, the term of this patent is extended or adjusted under 35 U.S.C. 154(b) by 252 days.

(21) Appl. No.: 15/782,496

(22) Filed: Oct. 12, 2017

(65) Prior Publication Data

US 2019/0114393 A1 Apr. 18, 2019

(51) Int. Cl.
*A61N 1/372* (2006.01)
*A61B 5/04* (2006.01)
(Continued)

(52) U.S. Cl.
CPC ...... *G06F 19/3418* (2013.01); *A61B 5/04014* (2013.01); *A61B 5/04017* (2013.01);
(Continued)

(58) Field of Classification Search
CPC ............. G06F 19/3418; A61B 5/04014; A61B 5/04017; A61B 5/07464; A61B 5/686; A61B 5/6869; A61B 5/725; A61N 1/025; A61N 1/3702; A61N 1/372; A61N 1/3962; G61H 40/63
(Continued)

(56) References Cited

U.S. PATENT DOCUMENTS 7,113,589 B2 9/2006 Mitchler
7,623,914 B1 11/2009 Andersen et al.
(Continued)

FOREIGN PATENT DOCUMENTS

WO 2017089803 A1 11/2009

OTHER PUBLICATIONS

International Preliminary Report on Patentability for corresponding PCT Application No. PCT/US2018/055210 dated Apr. 23, 2020.

*Primary Examiner* — Mallika D Fairchild
*Assistant Examiner* — Minh Duc G Pham
(74) *Attorney, Agent, or Firm* — The Small Patent Law Group LLC; Dean D. Small

(57) ABSTRACT

An implantable medical device and method are provided for comprising a sensing circuit that is configured to sense and output physiologic data indicative of a physiologic characteristic of a patient and at least one processor. A memory is coupled to the at least one processor. The memory stores program instructions and processed data. The program instructions are executable by the at least one processor to execute general operational functions within the IMD. A hybrid signal processing (HSP) circuit is coupled to the at least one processor and the sensing circuit. The HSP circuit is adapted to filter the physiologic data. The HSP circuit comprises a plurality of first order filters, a plurality of higher order filters, and a switch matrix that is configured to interconnect a combination of the first and higher order filters to form a hybrid digital filter having a select composite frequency response that utilizes no more than a select power demand.

20 Claims, 8 Drawing Sheets

(51) Int. Cl.
- *A61B 5/00* (2006.01)
- *A61B 5/0464* (2006.01)
- *A61N 1/37* (2006.01)
- *A61N 1/39* (2006.01)
- *G06F 19/00* (2018.01)
- *G06F 1/3203* (2019.01)
- *A61N 1/02* (2006.01)
- *G16H 40/63* (2018.01)
- *G01R 23/167* (2006.01)

(52) U.S. Cl.
CPC ............ *A61B 5/0464* (2013.01); *A61B 5/686* (2013.01); *A61B 5/6869* (2013.01); *A61B 5/725* (2013.01); *A61N 1/025* (2013.01); *A61N 1/372* (2013.01); *A61N 1/3702* (2013.01); *G16H 40/63* (2018.01); *A61B 2560/0209* (2013.01); *A61N 1/3962* (2013.01); *G01R 23/167* (2013.01); *G06F 1/3203* (2013.01)

(58) Field of Classification Search
USPC .......................................................... 600/509
See application file for complete search history.

(56) References Cited

U.S. PATENT DOCUMENTS

| | | | |
|---|---|---|---|
| 2007/0265537 A1* | 11/2007 | Lee | A61B 5/04017 600/509 |
| 2008/0033499 A1 | 2/2008 | Boileau et al. | |
| 2016/0287870 A1* | 10/2016 | Yip | A61N 1/36038 |

* cited by examiner

HYBRID SIGNAL PROCESSING CIRCUIT FOR IMPLANTABLE MEDICAL DEVICES AND METHODS

BACKGROUND

Embodiments of the present disclosure generally relate to methods and devices that utilize hybrid signal processing circuits to process signals sensed by implantable medical devices.

An implantable medical device (IMD) is an apparatus, driven by a power source, which is implanted in a patient to monitor, detect, and possibly affect biological signals in the patient. Implantable medical devices include, but are not limited to, implantable cardiac, rhythm management devices, neurostimulation devices, implantable pressure transducers, and implantable drug delivery devices.

Many IMDs are configured to sense various types of physiologic data. For example, cardiac rhythm management devices sense intra-cardiac electrocardiograms (IEGMs), while neurostimulation devices (e.g., deep brain stimulation systems) may sense electrocorticograms (ECoGs) or local field potentials (LPF). In general, the physiologic data is sensed by sensing circuits that are connected to one or more sets of electrodes connected to the body. The sensing circuits, among other things, amplify and process signals of interest, while rejecting or filtering out signals that are not of interest (e.g., outside of a frequency band of interest). The amplified and processed signals that are output by the sensing circuit are then analyzed for other features of interest and/or stored for later recall. The sensing circuitry is typically implemented in a hardware configuration (in lieu of signal processing on a general purpose device processor) to reduce power consumption of the sensing operations.

SUMMARY

In accordance with embodiments herein, an implantable medical device is provided. The device comprises a sensing circuit that is configured to sense and output physiologic data indicative of a physiologic characteristic of a patient and at least one processor. A memory is coupled to the at least one processor. The memory stores program instructions and processed data. The program instructions are executable by the at least one processor to execute general operational functions within the IMD. A hybrid signal processing (HSP) circuit is coupled to the at least one processor and the sensing circuit. The HSP circuit is adapted to filter the physiologic data. The HSP circuit comprises a plurality of first order filters, a plurality of higher order filters, and a switch matrix that is configured to interconnect a combination of the first and higher order filters to form a hybrid digital filter having a select composite frequency response that utilizes no more than a select power demand.

Optionally, the first order filters may represent digital integer filters that may be programmed utilizing integer coefficients. The higher order filters may represent second order recursive digital filters. The higher order digital filters may represent bi-quadratic digital filters, at least a portion of which have different corresponding frequency passbands. The plurality of first order filters may include low-pass integer filters with different corresponding low-pass frequency ranges and high-pass integer filters with different corresponding high-pass frequency ranges. The switch matrix may interconnect at least a portion of the low-pass integer filters, high-pass integer filters and bi-quadratic filters in a cascaded manner to form the hybrid filter having the select composite frequency response. The switch matrix may be configured to interconnect at least a portion of the plurality of first order filters and the plurality of higher order filters in a cascading manner to form the select composite frequency response.

Optionally, the switch matrix may be configured to interconnect at least a portion of the plurality of first order filters and the plurality of higher order filters in a cascading manner to define a hybrid digital filter that utilizes no more than a select power demand. The switch matrix may be configured to interconnect at least one of the first order filters and at least one of the higher order filters in one of an additive or subtractive manner to form the select composite frequency response. The at least one of the higher order filters may be configured as a wideband low-pass filter. The at least one of the first order filters may be configured as a narrowband low-pass filter. The narrowband low-pass filter may have a cutoff frequency below a cutoff frequency of the wideband low-pass filter. At least one of the higher order filters may be configured to have a frequency response exhibiting a first attenuation rate in a corresponding transition region and wherein at least one of the first order filters is configured to have a frequency response exhibiting a second attenuation rate in a corresponding transition region, the first attenuation rate being greater than the second attenuation rate.

In accordance with embodiments herein, a method of processing data in an implantable medical device (IMD) is provided. The method utilizes a hybrid signal processing (HSP) circuit that has a select composite frequency response that utilizes no more than a select power demand. The HSP circuit defines the select composite frequency response by interconnecting a combination of one or more first order filters from a plurality of first order filters and one or more higher order filters from a plurality of higher order filters. The method senses physiologic data at a sensing circuit. The physiologic data is indicative of a physiologic characteristic of a patient. The method further filters the physiologic data at the HSP circuit utilizing the select composite frequency response to provide filtered physiologic data.

Optionally, the method may comprise at least one of processing or storing the filtered physiologic data. The method may comprise programming integer filters utilizing integer coefficients to define the plurality of first order filters in the HSP circuit. The method may provide second order recursive digital filters as the plurality of higher order filters in the HSP circuit. The method may configure bi-quadratic digital filters as the higher order filters. The biquadratic digital filters may have different corresponding frequency passbands or cutoff frequencies. The method may configure the plurality of first order filters as low-pass integer filters with different corresponding low-pass frequency ranges and as high-pass integer filters with different corresponding high-pass frequency ranges and may interconnect at least a portion of the low-pass integer filters, high-pass integer filters and bi-quadratic filters in a cascaded manner to form the hybrid filter having the select composite frequency response.

Optionally, the method may configure the plurality of first order filters as low-pass integer filters with different corresponding low-pass frequency ranges and as high-pass integer filters with different corresponding high-pass frequency ranges and may interconnect at least a portion of the low-pass integer filters, high-pass integer filters and bi-quadratic filters in an additive or subtractive manner to form the hybrid filter having the select composite frequency response. The method may define the select composite frequency response based on a convolution of a frequency response of at least one of the plurality of first order filters and a frequency response of at least one of the plurality of higher order filters.

Optionally, the method may configure at least one of the higher order filters as a wideband low-pass filter and configuring at least one of the first order filters as a narrowband low-pass filter, the narrowband low-pass filter having a cutoff frequency below a cutoff frequency of the wideband low-pass filter. The method may configure at least one of the higher order filters to have a frequency response exhibiting a first attenuation rate in a corresponding transition region and configuring at least one of the first order filters to have a frequency response exhibiting a second attenuation rate in a corresponding transition region, the first attenuation rate being greater than the second attenuation rate.

DETAILED DESCRIPTION

Figure 1:
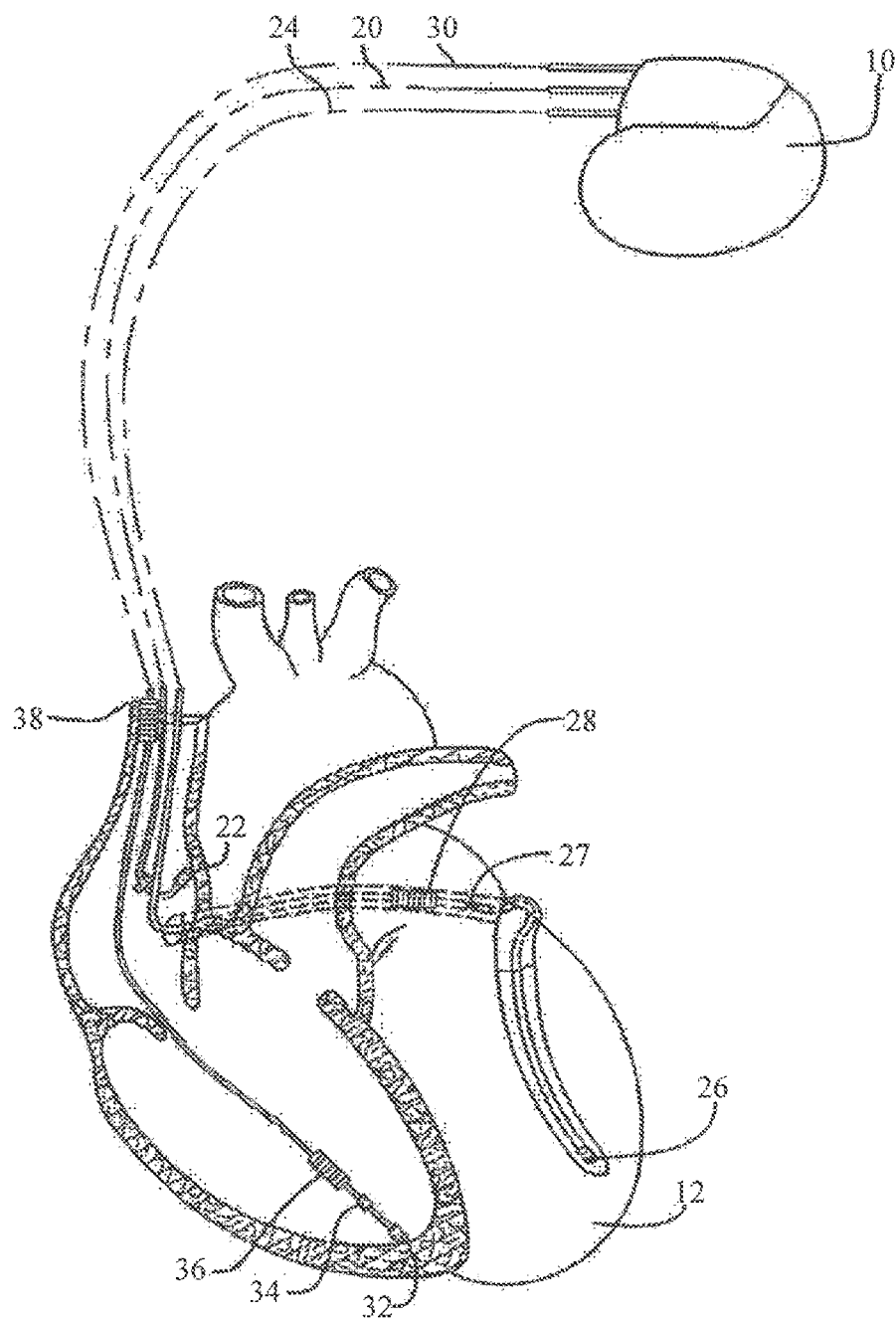
FIG. 1 illustrates an exemplary ICD in electrical communication with a patient's heart by way of three leads, suitable for delivering multi-chamber stimulation and pacing therapy in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in al least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods and devices described herein employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be reperformed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "integer filter" refers to a class of digital filters that have only integer coefficients in the z-domain transfer function that defines the filter.

The terms "order filter" and "filter order" are used interchangeably to refer to a number describing the highest exponent in the numerator or denominator of a z-domain transfer function that defines a digital filter. For example, a second order filter is defined by a transfer function, for which a second order exponent is the highest exponent in the numerator or denominator. For finite impulse response (FIR) filters, there is no denominator in the transfer function and the filter order is merely the number of taps used in the filter structure. For infinite impulse response (IIR) filters, the filter order is equal to the number of delay elements in the filter structure.

The term "first order filter" refers to digital filters that are characterized by a transfer function that has one pole and/or one zero, and that does not have two or more poles and/or two or more zeros. For example, a first order filter is defined by a transfer function, for which a first order exponent is the highest exponent in the numerator or denominator. One example of a first order filter is an integer filter. A first order filter may be configured as a high pass filter or a low-pass filter. When configured as a low-pass filter, the first order filter exhibits very little attenuation below a cutoff frequency.

The term "higher order filter" includes all digital filters that are not first order filters, including digital filters that are characterized by transfer functions that have two or more pops and/or two or more zeros (e.g., second order, third order or higher). For example, a second or third order filter is defined by a transfer function, for which a second or third order exponent, respectively, is the highest exponent in the numerator or denominator. One example of a higher order digital filter is a bi-quadratic or biquad filter. A bi-quadratic filter may be referred to as a second order recursive linear filter containing two poles and two zeros.

The terms "attenuate" and "attenuation" refers to an amplitude loss, usually measured in decibels (dB), incurred by a signal after passing through a digital filter. Filter attenuation is the ratio, at a given frequency, of the signal amp/hide at the output ($a_{output}$) of the filter over the signal amplitude at the input ($a_{input}$) of the filter, defined as: Attenuation (dB)=$20 \log_{10}(a_{output}/a_{input})$. For a given frequency, when the output amplitude of the filter is smaller than the input amplitude, the ratio $a_{output}/a_{input}$ is less than one and the attenuation becomes a negative number.

The terms "cascade" and "cascaded filters" are used interchangeably to refer to an implementation of a filtering system where multiple individual digital filters are connected in series. In a cascade configuration, the output of one filter drives the input of the following filter.

The term "cutoff frequency" refers to an upper passband frequency for low-pass filters, and a lower passband frequency for high-pass filters. For example, a cutoff frequency may be determined by a point at which the frequency response exhibits a select amount of attenuation, such as the −3 dB point of a filter magnitude response relative to a peak passband value.

The term "filter coefficients" refers to a set of constants, also called tap weights, used to multiply against delayed signal sample values within a digital filter structure. The filter coefficients define the desired filter frequency response. For a finite impulse response (FIR) filter, the filter coefficients are the impulse response of the filter.

The terms "frequency response" and "frequency magnitude response" are used interchangeably to refer to a frequency domain description of how a filter interacts with input signals. The frequency response may be characterized as a curve of filter attenuation (in dB) vs frequency.

The term "rolloff" refers to the steepness, or slope, of the filter response in the transition region from the passband to the stopband. For example, a particular digital filter may be said to have a rolloff of 12 dB/octave—meaning that the first octave of a frequency $f_0$, or $2f_0$, would be attenuated by 12 dB more than the filter attenuation at $f_0$. The second octave, $4f_0$, would be attenuated by 24 dB more than the filter attenuation at $f_0$, and so on.

The term "stopband" refers to a band of frequencies attenuated by a digital filter by a predetermined amount, such that the output signal at the corresponding frequencies within the stopband do not detract from or otherwise impact downstream processing. By way of example, the stopband may include ail frequencies, for which the output signal is attenuated by a −20 dB or more. Stopband attenuation is measured between a peak passband amplitude and the largest stopband lobe amplitude.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure in An Implantable Medical Device" and U.S. Pat. No. 9,232,485 "System And Method For Selectively Communicating With An Implantable Medical Device", which are hereby incorporated by reference.

Implantable Medical Device

The following detailed description of the accompanying drawings illustrates example embodiments of an implantable medical device (IMD) for efficient data processing. Other embodiments are possible, and modifications may be made to the embodiments within the spirit and scope of the IMD presented herein. Therefore, the following detailed description is not meant to limit the IMD. Rather, the scope of the IMD is defined by the appended claims.

It would be apparent to one of skill in the art that the IMD, as described below, may be implemented in many different embodiments of hardware, software, firmware, and/or the entities illustrated in the Figures. Any actual software and/or hardware described herein is not limiting of the IMD presented herein. Thus, the operation and behavior of the IMD will be described with the understanding that modifications and variations of the embodiments are possible, given the level of detail presented herein.

The IMD presented herein is particularly useful in the environment of an implantable cardioverter defibrillator (ICD). An ICD is a medical device that is implanted in a patient to monitor the electrical activity of a heart and to deliver appropriate electrical therapy: for example, pacing pulses, cardioverting pulses, or defibrillating (or shock) pulses, as required. The term "implantable cardioverter defibrillator" or simply "ICD" is used herein to refer to any implantable cardiac device known in the art. Hereinafter, the IMD apparatus presented shall be described in the environment of an ICD. It should be noted that the IMD defined by the appended claims is not limited to use solely in an ICD, but is described in an environment of an ICD for simplicity.

FIG. 1 illustrates an exemplary ICD 10 in electrical communication with a patient's heart 12 by way of three leads 20, 24 and 30, suitable for delivering multi-chamber stimulation and pacing therapy. To sense atrial cardiac signals, and to provide right atrial chamber stimulation therapy, ICD 10 is coupled to it right atrial lead 20, having at least an atrial tip electrode 22, which typically is implanted in the patient's right atrial appendage.

To sense left atrial and ventricular cardiac signals, and to provide left-chamber pacing therapy, ICD 10 is coupled to "coronary sinus" lead 24. Lead 24 is designed for placement in the "coronary sinus region," via the coronary sinus, for positioning of a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus. Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shock therapy using at least a left atrial coil electrode 28.

ICD 10 is also shown in electrical communication with the patient's heart 12 by way of an implantable right ventricular (RV) lead 30 having, in this embodiment, a RV tip electrode 32, a RV ring electrode 34, a RV coil electrode 36, and a superior vena cava (SVC) coil electrode 38. Typically, RV lead 30 is transvenously inserted into heart 12 so as to piece the RV tip electrode 32 in the right ventricular apex so that RV coil electrode 36 will be positioned in the right ventricle and SVC coil electrode 38 will be positioned in the superior vena cava. Accordingly, RV lead 30 is capable of receiving cardiac signals and delivering stimulation in the form of pacing and shock therapy to the right ventricle. Other embodiments of ICD 10 may include a single electrode and lead or one or more alternative combinations of the above mentioned electrode and lead configurations.

Amongst other things, any one of, or any combination of, leads 20, 24, and 30, functions as a sense circuit to sense an electrogram (EGM) signal from the heart 12. The EGM signal is then processed within the ICD 10, as discussed below. The sense circuit, with respective electrodes, thereby serves as means for sensing one or more electrical signals from the patient's heart 12. Further, any one of, or any combination of the leads 20, 24, and 30, in part, function as a therapy circuit to deliver a selected electro therapy to the heart 12. The therapy circuit, with respective electrodes, thereby serves as means for delivering an electro-therapy to the heart 12.

The selected electro-therapy can be, but is not limited to, anti-tachycardia pacing (ATP) therapy, or shock therapy. If ATP therapy is selected, a pre-programmed series of burst pulses is sent to the heart through any one of, or any combination of, leads 20, 24, and 30. There are several different ATP modalities which have been suggested for termination of tachycardia. Some examples of patent documents which discuss ATP therapies are U.S. Pat. Nos. 6,731,982, 4,408,606, 4,398,536, 4,488,553, 4,488,554, 4,390,021, 4,181,133 and 4,280,502, the disclosures of which are hereby incorporated in their entireties by reference.

Figure 2A:
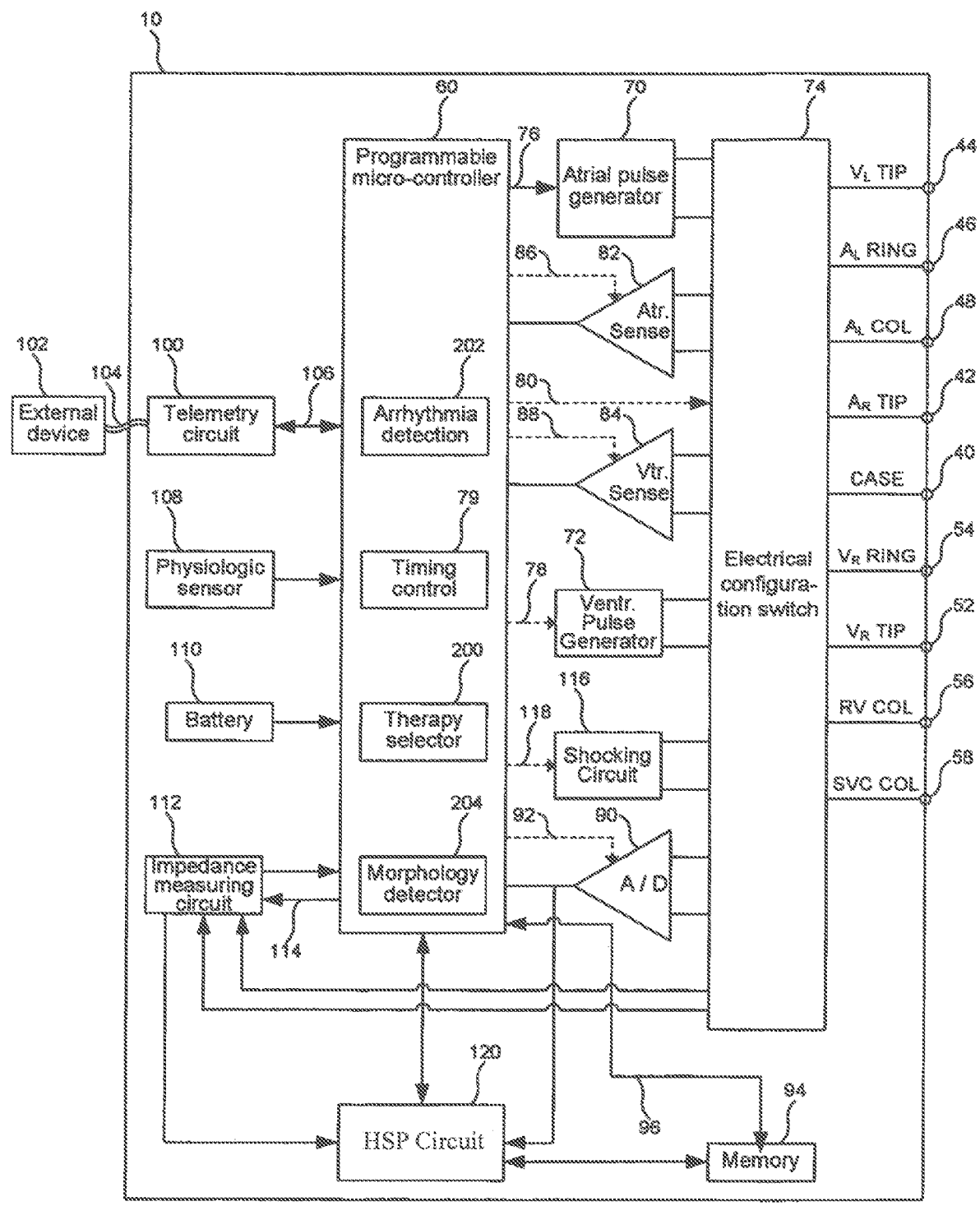
FIG. 2A shows a simplified block diagram of IMD, which is capable of treating both fast and slow arrhythmias with stimulation therapy, including cardioversion, defibrillation, and pacing stimulation in accordance with embodiments herein.

FIG. 2A shows a simplified block diagram of IMD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes 28, 36, and 38, for shocking purposes. Housing 40 further includes a connector (not shown) having a plurality of terminals 42, 44, 46, 48, 52, 54, 56, and 58. These terminals are shown schematically and, for convenience, the names of the electrodes to which they are connected are shown next to the terminals. For example, to achieve right atrial sensing and pacing, the connector includes a right atrial tip terminal ($A_R$ TIP) 42 adapted for connection to atrial tip electrode 22.

To achieve left chamber sensing, pacing, and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to left ventricular tip electrode 26, left atrial ring electrode 27, and left atrial coil electrode 28, respectively.

To support right chamber sensing, pacing, and shocking the connector also includes a right ventricular tip terminal ($V_R$ TIP) 52, a right ventricular ring terminal ($V_R$ RING) 54, a right ventricular shocking terminal (RV COL) 56, and an SVC shocking terminal (SVC COIL) 58, which are configured for connection to right ventricular tip electrode 32, right ventricular ring electrode 34, RV coil electrode 36, and SVC coil electrode 38, respectively.

A programmable microcontroller 60 controls the various modes of stimulation therapy. The microcontroller 60 typically includes a microprocessor, or equivalent control circuitry, designed specifically for controlling the delivery of stimulation therapy and can further include RAM or ROM memory, logic and timing circuitry, state machine circuitry, and 110 circuitry. The details of the design of microcontroller 60 are not critical to the present invention. Rather, any suitable microcontroller 60 can be used to carry out the functions described herein.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within ICDs, and their inter-relationship, see U.S. Pat. No. 4,788,980 (Mann et al.). The '052, '555, '298 and '980 patents are incorporated herein by reference in their entireties.

Microcontroller 60 includes a timing control circuitry 79, which is used to control pacing parameters (e.g., the timing of stimulation pulses, the burst pacing parameters, etc.) as well as to keep track of the timing of refractory periods, post ventricular atrial refractory period intervals, noise detection windows, evoked response windows, alert intervals, marker channel timing, etc., which are well known in the art. Examples of pacing parameters include, but are not limited to, atrio-ventricular delay, interventricular delay, atrial inter-conduction delay, ventricular interconduction delay, and pacing rate.

Microcontroller 60 also includes a therapy selector unit 200, which serves as means for selecting an appropriate electro therapy for delivery to the heart. The appropriate therapy can be selected from a plurality of therapies. For example, ATP therapy can be used. Alternative therapies include shock therapy, or any other electro therapies known in the art.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Switch block 74 includes a plurality of switches for connecting the desired electrodes to the appropriate I/O circuits, thereby providing complete electrode programmability. Accordingly, switch block 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch block 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch block 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60, which in turn is able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84.

For arrhythmia detection, ICD 10 utilizes the atrial and ventricular sensing circuits 82 and 84 to retrieve EGM signals from the heart. The EGM signals are then analyzed in the arrhythmia detection unit 202 of the microcontroller 60. If an arrhythmia is detected, typically based on heart rate, the arrhythmia can then be classified by morphology detector unit 204.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing in microcontroller 60, and/or telemetric transmission to an external device 102. Data acquisition system 90 is coupled to right atrial lead 20, coronary sinus lead 24, and right ventricular lead 30, through switch 74, to sample cardiac signals across any pair of desired electrodes.

Advantageously, data acquisition system 90 can be coupled to microcontroller 60, HSP circuit 120, or other detection units, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 80, and enabling data acquisition system 90, via a control signal 92, to sample the cardiac signal that falls in the capture detection window and, based on the amplitude, determine if capture has occurred.

The IMD 10 includes a hybrid signal processing (HSP) circuit 120 that is coupled to the microcontroller 60 and the sensing circuitry. The HSP circuit 120 is adapted to filter physiologic data sensed by the sensing circuitry. As explained hereafter, the HSP circuit comprises a plurality of first order filters, a plurality of higher order filters, and a switch matrix configured to interconnecting a combination of the first and higher order filters to form a hybrid digital filter having a select composite frequency response that utilizes no more than a select power demand. The first order filters may represent digital integer filters that are programmed utilizing integer coefficients. The higher order filters may represent second order recursive digital filters. As a further example, the higher order digital filters may represent bi-quadratic digital filters, at least a portion of which have different corresponding frequency passbands. In accordance with embodiments herein, the plurality of first order filters include low-pass integer filters with different corresponding low-pass frequency ranges and high-pass integer filters with different corresponding high-pass frequency ranges.

The implementation of capture detection circuitry and algorithms are well known. See for example, U.S. Pat. No. 4,729,376 (Decote, Jr.); U.S. Pat. No. 4,708,142 (Decote, Jr.): U.S. Pat. No. 4,686,988 (Sholder); U.S. Pat. No. 4,969,467 (Callaghan et al.); and U.S. Pat. No. 5,350,410 (Mann et al.), which patents are hereby incorporated in their entireties herein by reference. The type of capture detection system used is not critical to the present invention.

Microcontroller 60 is further coupled to a memory unit 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to heart 12 within each respective tier of therapy. The memory unit 94 thus serves as means for "learning" which therapies are most effective under certain conditions. As such, when a condition repeats itself, the memory can recognize the condition and adapt the selected therapy to match the previously used successful therapy.

Advantageously, the operating parameters of ICD 10 may be non-invasively programmed into memory unit 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104. Telemetry circuit 100 also serves as a means for receiving parameters from an outside programmer, to thereby program the HSP circuit 120, via operation of microcontroller 60.

For examples of external devices, such as external device 102, see U.S. Pat. No. 4,809,697 (Causey, III et al.); U.S. Pat. No. 4,944,299 (Silvian); and U.S. Pat. No. 6,275,734 (McClure et al.); all patents being hereby incorporated in their entireties herein by reference.

Memory unit 94 is also coupled to HSP circuit 120. As such, HSP circuit 120 is adapted to receive data from memory unit 94, perform a signal processing function on the data, and return processed data to memory unit 94. Such operations are generally programmed and supervised by operation of microcontroller 60. In other words, microcontroller 60 can reconfigure the internal parameters of HSP circuit 120, to thereby modify the processing function of HSP circuit 120. As such, the microcontroller 60 serves as general processing means for executing general operational functions, while the HSP circuit 120 serves as reconfigurable signal processing circuit.

ICD 10 further includes a physiologic sensor 108 that can be used to detect changes in cardiac performance or changes in the physiological condition of the heart. Accordingly, microcontroller 60 can respond by adjusting the various pacing parameters (such as amplitude, rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 may further include a magnet detection circuitry (not shown), coupled to microcontroller 60. The magnet detection circuitry detects when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 is shown as having an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement, detecting operable electrodes and automatically switching to an operable pair if dislodgement occurs, measuring respiration or minute ventilation, measuring thoracic impedance for determining shock thresholds, detecting when the device has been implanted, measuring stroke volume, and detecting the opening of heart valves. The impedance measuring circuit 112 is advantageously coupled to switch 74 so that any desired electrode may be used. Impedance measuring circuit 112 is also coupled to HSP circuit 120, wherein outputs from impedance measuring circuit 112 can be processed and stored in memory unit 94. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. Shocking circuit 116 generates shocking pulses of low (up to about 0.6 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV coil electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2A.

Hybrid Signal Processing Circuits

Embodiments herein overcome certain disadvantages experienced by IMDs that filter sensed data utilizing analog filtering circuits. While analog filtering circuits utilize very low power, the analog filtering is based on a finite set of resistors and capacitors that are integrated into custom integrated circuits (ICs). A programmable frequency response of an analog filter circuit is achieved by selecting the set of resistors and capacitors that most closely matches the desired frequency response. When a custom IC is tuned to have a particular frequency response, and then the response frequency needs to be changed, the configuration of the resistors and capacitors must be modified on the IC circuit which represents a costly revision to the IC or related circuitry. Embodiments herein utilize digital filtering with programmable coefficients that determine the frequency response of the filter. The coefficients may be programmed based on the application, thereby accommodating a larger variation in the desired frequency response.

Embodiments herein overcome certain disadvantages experienced by IMDs that filter sensed data utilizing conventional digital filtering circuits. Digital filtering circuits cannot achieve any arbitrary frequency response. The frequency response of a digital filtering circuit is determined (and limited) by the number of digital bits that are utilized to define each data value to be filtered. The greater the number of digital bits processed by the filter circuit, the greater the numerical accuracy of the data that is filtered. As the number of digital bits (and accuracy) of the filter increases, the digital filter structures becomes larger in size due to the numerical representations (e.g., 8-bit, 16-bit, 32-bit words) in the filter. Also, the frequency response of a digital filtering circuit is determined (and limited) by the type or class of filter structure. Various classes of filter structures are available.

In accordance with embodiments herein, filter circuits are combined from two primary classes, namely first order filters and higher order filters (e.g., any filter order greater than one), to form a hybrid signal processing (HSP) circuit adapted to filter physiologic data. The HSP circuit comprises a plurality of first order filters, a plurality of higher order filters, and a switch matrix configured to interconnecting a combination of the first and higher order filters to form the hybrid digital filter. The hybrid digital filter is formed to provide a select composite frequency response while utilizing no more than a select power demand.

The higher order filters are provided with one or more select order(s) of digital filters. For example, the higher order digital filters may include a digital filter architecture that is a second order recursive filter, also referred to as a bi-quadratic or biquad fitter. Optionally, the higher order filters greater than second order may be utilized. Additionally or alternatively, higher order filters great than second order may be formed by cascading together multiple $2^{nd}$ order bi-quadratic filters. Additionally or alternatively, bi-quad filters may be cascaded together to create low-pass, high-pass, band-pass and band-stop frequency responses. Depending on how a bi-quad filter is implemented, each bi-quad filter may have 4, 5 or more multipliers and 4 or more adders. In accordance with embodiments herein, for at least some IMD applications, a sufficient numerical accuracy and signal resolution may be achieved utilizing a data channel widths of 8-16-bit. When utilizing 8 to 16 bit data channel width, a bi-quad filter can become a relatively large structure. The larger the structure, the higher the consumed power as power is proportional to the number of nodes that are switched/toggled within the filter during operation.

Figure 2B:
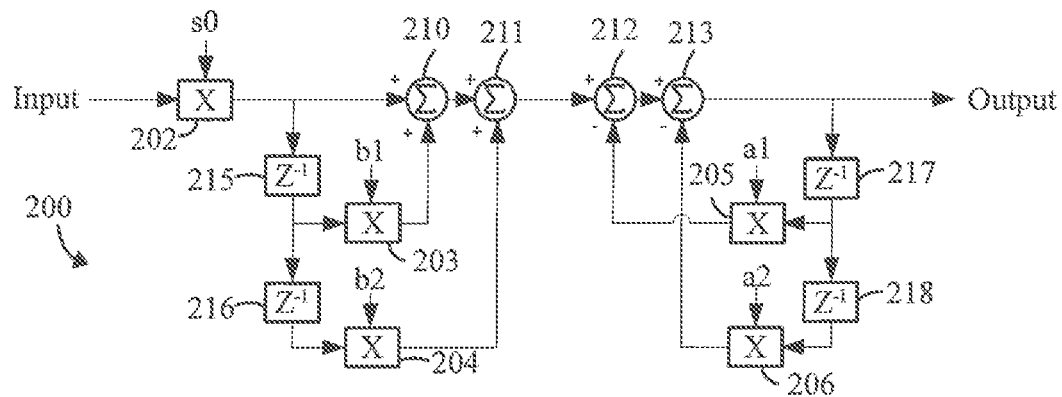
FIG. 2B illustrates a bi-quadratic filter formed in accordance with embodiments herein.

FIG. 2B illustrates a biquad filter 200 formed in accordance with embodiments herein. The filter 200 of FIG. 2B, includes a group of multipliers 202-206 that multiply input signals by corresponding coefficients (S0, B1, B2, A1, A2). The coefficients may be integers or non-integers. The filter 200 also includes a group of adders 210-213, and storage unit 215-218. The filter 200 of FIG. 2B corresponds to a single bit of a data channel, and thus is repeated for each additional bit of the data channel. The filter 200 has a two dimensional (2D) surface area that is dependent on the number of logic gates utilized to form the filter. The 2D surface area can be defined by the following formula that calculates the number of fundamental logic gates in the biquad filter, where w represents the data channel width (e.g., 8 bit, 16 bit, 32 bit):

$$A(w)=25w^2+20(w+1)+24w \quad \text{(Equation \#1)}$$

The first term coefficient (25) represents the area component that is attributable to the multipliers 202-206 in the biquad filter for one bit of the data channel. In the present example, a carry-ripple multiplier structure may be used with 5 multiplier logic components times 5 logic gates for each full adder (e.g., 5×5). The second term coefficient (20) represents the area component that is attributable to the logic gates from the adders 210-213 for one data channel. For example, for each full adder, the biquad filter will include 4 adders×5 logic gates. The last term coefficient (24) represents the area component that is attributable to the storage units 215-218. In the present example, 6 logic dements are provided per storage unit 215-218 for one bit of the data channel.

The power demand of the digital filter 200 is proportional to the size of the digital filter circuit. For example, the power demand is directly proportional to a number of nodes that toggle state, and a frequency at which the digital filter 200 toggles the node states. In an IMD, as the circuitry of the digital filter 200 increases the number of logic gates, the power consumption similarly increases which decreases the longevity of the IMD. Thus, a trade-off is presented between filter circuit complexity and power demand/consumption.

In accordance with embodiments herein, sensing circuits may be provided that utilize a data channel width of 8-12 bits and with typical node state switching frequencies between 250 and 5000 Hz, depending on the application. Optionally, the data channel width may utilize more than 8-12 bits within the filter in order to accommodate extra signal headroom. Table 1 below provides some non-limiting examples of areas and power demand/consumption based on the noted data channel widths and the state switching frequencies for a biquad filter. In Table 1, the power consumption estimates are based on the assumption that 50% of the logic gates within the filtering circuit are toggled at the noted frequency. Further, Table 1 assumes a certain power consumption per logic gate per megahertz (e.g., 20 nW/MHz). It is recognized that other power consumption amounts per gate may be utilized.

TABLE 1

| Data Channel Width (bits) | Minimum Number of Logic Gates | 250 Hz | 1000 Hz | 5000 Hz |
|---|---|---|---|---|
| 8 | 2000 | 5.0 nW | 20 nW | 75 nW |
| 12 | 4000 | 10 nW | 40 nW | 150 nW |
| 16 | 7000 | 20 nW | 70 nW | 300 nW |

In accordance with embodiments herein, multiple biquad filters may be connected together to create a select composite frequency response. As the number of channels increases, similarly, the filter grows in physical size and power demand. By way of example, for a typical cardiac rhythm management application, each sensing channel may utilize 3 biquad filters. Accordingly, a dual chamber IMD, may utilize a total of 6 biquad filters running at 250 Hz.

As shown in the above area formula (Equation #1), the largest size factor is the multiplication components. If the multiplication components were reduced or eliminated, the area and power demand would be substantially lower. In accordance with embodiments herein, a class of first order filters is utilized that does not require explicit multipliers. For example, embodiments may utilize integer filters as the first order filters. Integer filters are physically much smaller and demand lower power as compared to higher order filters such as biquad digital filters. A drawback of integer filters is that integer filters are designed generally to be dedicated to either a low-pass or high-pass frequency range and are not readily programmable to frequency responses having relatively tight attenuation tolerances. In integer filters, multiplication operations are performed utilizing data shifting, not explicit with multiplication components. As a result, the coefficients of the integer filters are limited to powers of 2 or additions/subtractions of powers of two.

Figure 2C:
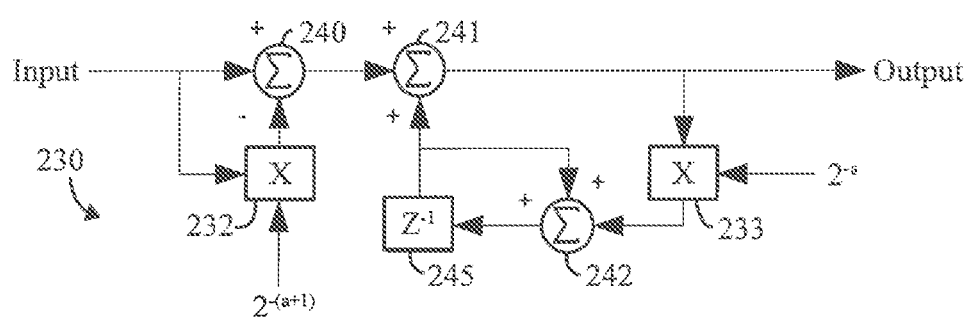
FIG. 2C illustrates an example configuration for an integer filter that is designed as a first order high-pass filter in accordance with embodiments herein.
Figure 2D:
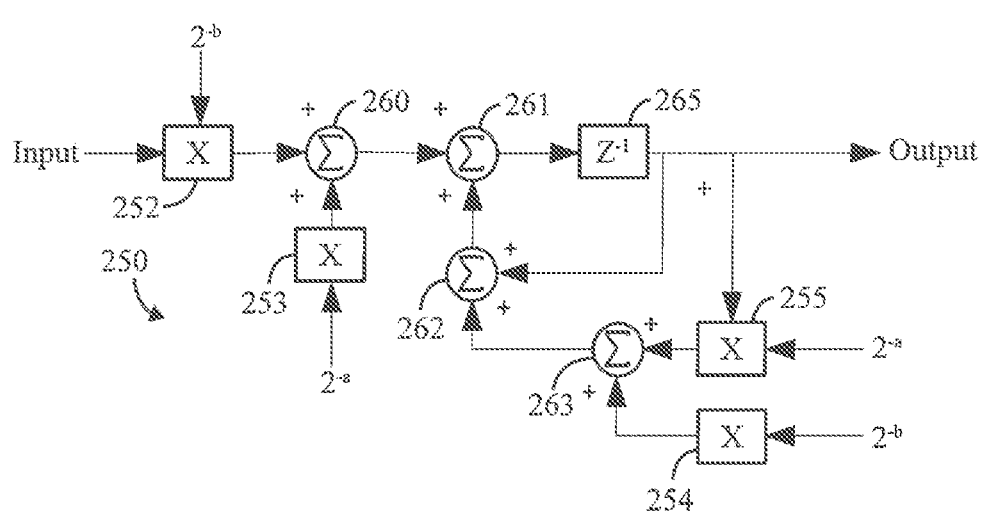
FIG. 2D illustrates an example configuration for an integer filter that is designed as a first order low-pass filter in accordance with embodiments herein.

FIG. 2C illustrates an example configuration for an integer filter 230 that is designed as a first order high-pass filter in accordance with embodiments herein. FIG. 2D illustrates an example configuration for an integer filter 250 that is designed as a first order low-pass filter in accordance with embodiments herein. The integer filter 230 includes shifting components 232-233, adders 240-242 and a storage unit 245. The integer filter 250 includes shifting components 252-255, adders 260-263 and a storage unit 265. While FIGS. 2C and 2D include logical symbols indicative of multipliers, it is recognized that the representative multiplication operations are performed by the shifting components 252-255 as arithmetic shifts of the binary point by an amount defined by the corresponding coefficients (−a, −b, −(a+1)). For example, when a coefficient is −1, the corresponding shifting component which shifts the binary point to the left by one, corresponding to a divide by two operation. When a coefficient is 2, the corresponding shift component which of the binary point to the right by two binary positions, corresponding to a multiply by four operation. The filters 230 and 250 correspond to a single bit of a data channel, and thus are repeated for each additional bit within the data channel width.

For integer filter configurations such as illustrated in FIGS. 2C and 2D, the following formula in equation 2 may be utilized to estimate the two dimensional area of the high-pass and low-pass integer filters, in order to compare equivalent orders of filters, the formula in Equation #2 assumes two cascaded filters:

$$A(w) = 40(w+1) + 12w \quad \text{(Equation \#2)}$$

in the foregoing equation, there is no coefficient attributable to multiplier logic components, such as in a biquad or higher order filter. The first term coefficient (40) represents the area component that is attributable to the logic gates from the adders (240-242 or 260-263) for one data channel. The last term coefficient (12) represents the area component that is attributable to the storage elements (245 or 265).

Table 2 provides non-limiting examples of area and power consumption for an integer filter based on the noted data channel widths and the state switching frequencies. In Table 2, the power consumption estimates are based on the assumption that 50% of the logic gates within the filtering circuit are toggled at the noted frequency. Further, Table 2 assumes a certain power consumption per logic gate per megahertz (e.g., 20 nW/MHz). It is recognized that other power consumption amounts per gate may be utilized.

TABLE 1

| Data Width | Minimum Number of Logic Gates | 250 Hz | 1000 Hz | 5000 Hz |
|---|---|---|---|---|
| 8 | 400 | 1.0 nW | 4.0 nW | 20 nW |
| 12 | 600 | 1.5 nW | 6.0 nW | 25 nW |
| 16 | 800 | 2.0 nW | 9.0 nW | 35 nW |

It is recognized that the numeric values in Tables 1 and 2 are approximate examples and are not limiting in any manner. When comparing Tables 1 and 2, it can be seen that substantial power savings occurs when utilizing integer filters (where possible) instead of biquad filters. For example, if a 16-bit integer filter can be used to replace an equivalent biquad filter operating at 250 Hz, the resulting filter circuit would represent over a 90% reduction in power (2 nW versus 20 nW). For example, if a 12-bit integer filter were used to replace an equivalent biquad filter operating at 1000 Hz, the resulting filter circuit would represent an 85% reduction in power (6 nW versus 40 nW).

Figure 2E:
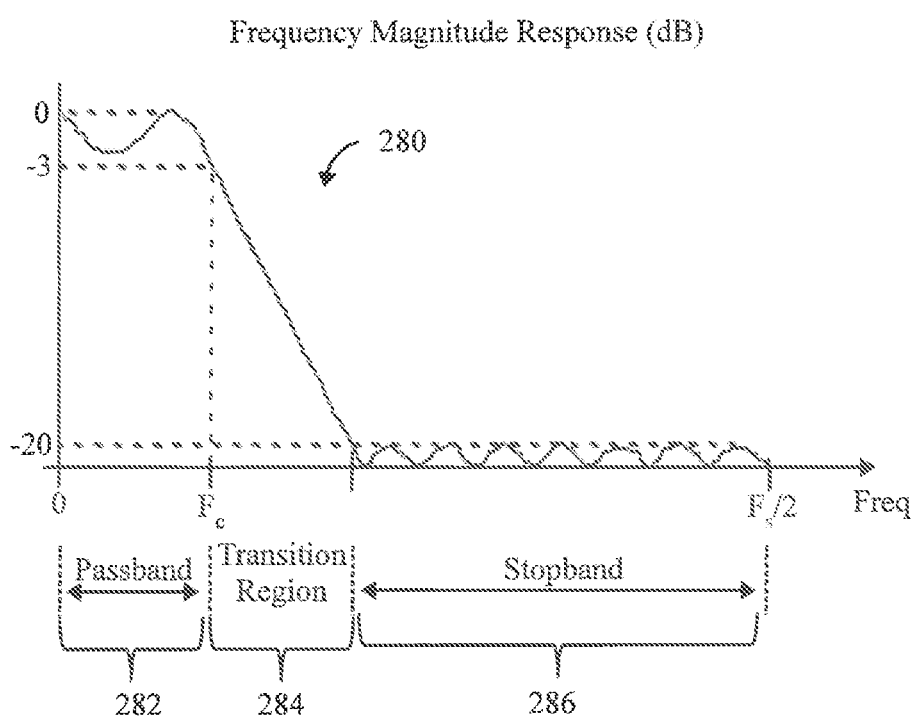
FIG. 2E illustrates an example of a frequency magnitude response that may be exhibited by a low-pass digital filter in accordance with embodiments herein.

FIG. 2E illustrates an example of a frequency magnitude response 280 that may be exhibited by a low-pass digital filter. The frequency response 280 plots attenuation along the vertical axis (from zero down to −20 dB) and frequency along the horizontal axis. The frequency response 280 includes a passband 282, for which the input signal experiences very little attenuation by the filter before being output. The frequency response 280 has a transition region 284 over which the filter progressively attenuates the input signal more at successively higher frequencies until reaching a stopband 286. A cutoff frequency $f_c$ is noted at the transition between the passband 282 and the transition region 284. Frequencies in the stopband 286 are attenuated by a predetermined amount (e.g., −20 dB).

Figure 4:
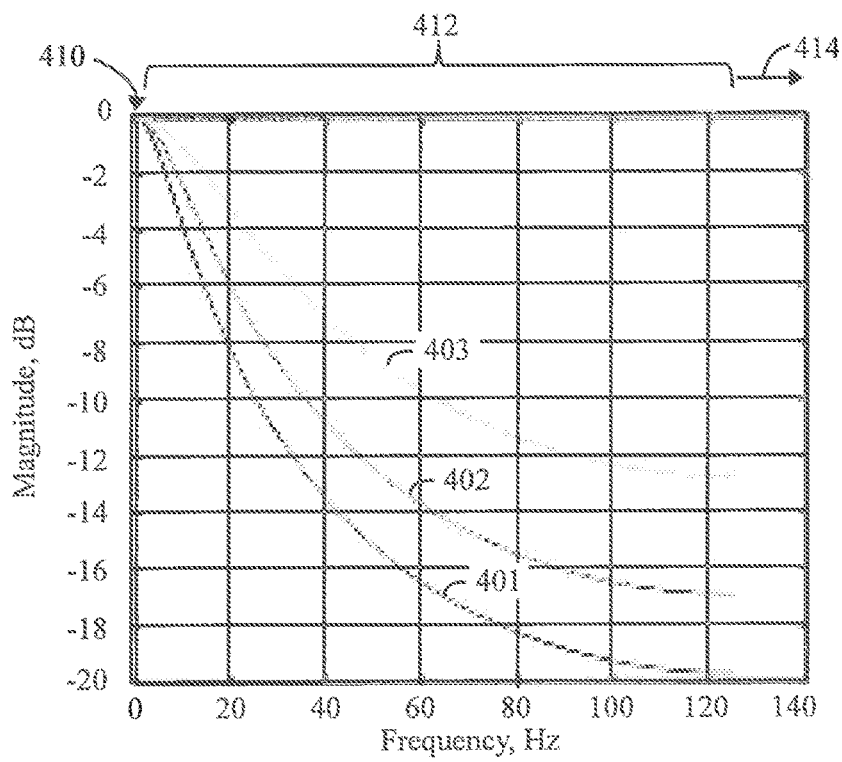
FIG. 4 shows an example of potential different low-pass filter frequency responses for three consecutive values of the "a" coefficient, such as utilized by the first order low-pass filter of FIG. 2D in accordance with embodiments herein.

FIG. 4 shows an example of potential different low-pass filter frequency responses 401-403 for three consecutive values of the "a" coefficient (e.g., 1, 2, 3), such as utilized by the first order low-pass filter 250 of FIG. 2D. In the example of FIG. 4, a very small passband 410 (e.g., 1-3 Hz) is provided, followed by a relatively long transition region 412 (e.g., 3-120 Hz), followed by a stopband 414 (e.g., greater than 120 Hz). As shown in FIG. 4, the transition region extends over a relatively long frequency range and transitions at a relatively slow attenuation rate. Within the transition region 412, the attenuation rate of the frequency response 401 is substantially steeper (has a larger negative slope) as compared to the attenuation rate of the frequency responses 402, 403. For example, the frequency response 401 exhibits an attenuation of 0 to −16 dB over the frequency range of 3 Hz to 55 Hz. Within the same frequency range of 3 Hz to 55 Hz, the frequency responses 402 and 403 exhibits an attenuation of approximately −13 dB and −9 dB, respectively. Further, the frequency responses 402 and 403 do not achieve an attenuation of a −20 dB until substantially after a 120 Hz frequency. At 120 Hz, the frequency responses 401-403 exhibit substantially different attenuation levels, namely approximately −20 dB, −17 dB and −13 dB, respectively. Incrementing the "a" coefficient of the filter transfer function by a single integer value changes the characteristics (e.g., attenuation rate, length of the transition region, cutoff frequency for the stopband) of the frequency responses 401-403. As shown in FIG. 4, the low-pass cut-off frequency, attenuation rate, length of the transition region, cutoff frequency for the stopband and other characteristics are programmable but in a somewhat coarse manner as compared to the frequency response characteristics exhibited by higher order digital filters.

Integer filters are not readily programmable to two exhibit frequency response characteristics that have narrow tolerances, given that integer filters only utilize integer coefficients when defining characteristics of the frequency response. Limiting a filter to the use of integer coefficients restricts the available characteristics of the frequency response.

In accordance with embodiments herein, hybrid signal processing circuits are formed that cascade higher order filters with first order filters to form a composite frequency response that is determined by the convolution of individual filter coefficients. The convolution shifts the high-pass and low-pass cutoff frequencies of the individual filters to form a composite high-pass cutoff frequency and composite low-pass cutoff frequency. The hybrid signal processing circuits herein use the coarse integer filters for the wide range filtering and the higher order filters for the fine frequency tuning, thereby creating a composite frequency response from a combination of integer and a higher order filters, where the combination exhibits a lower power demand than would be achieved by a filter system using only higher order filters.

Figure 3:
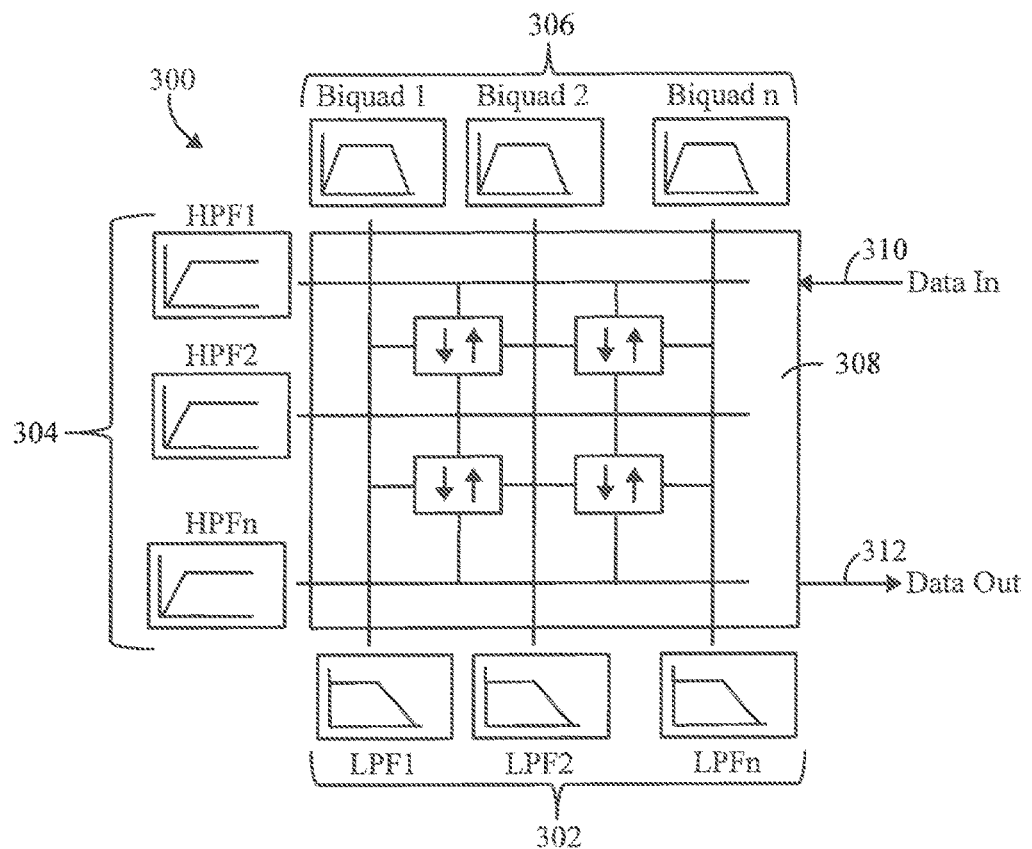
FIG. 3 illustrates an HSP circuit formed in accordance with an embodiment herein.

FIG. 3 illustrates an HSP circuit 300 formed in accordance with an embodiment herein. The HSP circuit 300 includes a plurality of first order filter circuits 302 and 304, and a plurality of higher order filter circuits 306. For example, the first order filter circuits 302 are configured to have different corresponding low-pass filter frequency ranges (as denoted by LPF1-LPFn). The first order filter circuits 304 are configured to have different corresponding high-pass frequency ranges (as denoted by HPF1-HPFn). The higher order filter circuits 306 are configured to have different corresponding passbands (as denoted at biquad1 to biquad3).

The HSP circuit 300 includes a switch matrix 308 that selectively and re-configurability interconnects various combinations of the first and higher order filter circuits 302-306. The switch matrix 308 includes a data input 310 and data output 312. The data input 310 receives digitized physiologic data from various sources, such as directly from an A/D converter, the sensing circuits and/or memory. The data output 312 supplies the processed (e.g., filtered) physiologic data to various other circuits within the IMD, such as a main processor, memory, and the transceiver and the like.

The switch matrix 308 includes sample rate converters that are configured to down sample or up sample the physiologic data received from the data input 310. For example, it may be desirable to down sample incoming data to reduce the data rate, such as in connection with storing a continuous recording of physiologic data associated with an arrhythmic episode. As another example, it may be desirable to up sample incoming data to increase the data rate such as in connection with analysis of characteristics of interest within the physiologic data (e.g., analyzing the shape or morphology of segments in the data, analyzing peaks or valleys in the data and the like).

As described herein, the HSP circuit 300 provides a re-configurable network in which a variety of filters can be interconnected to achieve the select frequency response but at a much lower power as compared to a standard filter architecture. The switch matrix 308 allows the physiologic data be directed into any number of available first and/or higher order filter circuits 302-306 and directs the outputs of the first and/or higher order filter circuits 302-306 to the inputs of other first and/or higher order filter circuits 302-306 or to the matrix data output 312.

In accordance with embodiments herein, the switch matrix 308 may interconnect combinations of a common type of first and/or higher order filter circuit 302-306 in a cascaded order. The first and/or higher order filter circuits 302-306 that are not used are not state switching and therefore do not consume power. Once the physiologic data is filtered using a select combination of the first and/or higher order filter circuits 302-306. The first order filter circuits 302, 304 may be configured as low power coarse filters (either low-pass, or high-pass), while the higher order filter circuits 306 may be configured as high power fine adjustment biquad filters. It is recognized that, the number of each type of filter circuit 302-306 can vary depending on the application and available area within the IMD.

The switch matrix 308 interconnects at least a portion of the low-pass integer filters, high-pass integer filters and bi-quadratic filters in a cascaded manner to form the hybrid filter having the select composite frequency response. The switch matrix 308 is configured to link at least a portion of the plurality of first order filters 302, 304 and the plurality of higher order filters 306 in a cascading manner to form the select composite frequency response. The switch matrix 308 is configured to link at least a portion of the plurality of first order filters 302, 304 and the plurality of higher order filters 306 in a cascading manner to define a hybrid digital filter that utilizes no more than a select power demand. The switch matrix 308 is configured to interconnect at least one of the first order filters 302, 304 and at least one of the higher order filters 306 in one of an additive or subtractive manner to form the select composite frequency response, wherein the at least one of the higher order filters is configured as a wideband low-pass filter and wherein the at least one of the first order filters is configured as a narrowband low-pass filter, the narrowband low-pass filter having a cutoff frequency below a cutoff frequency of the wideband low-pass filter.

Figure 5:
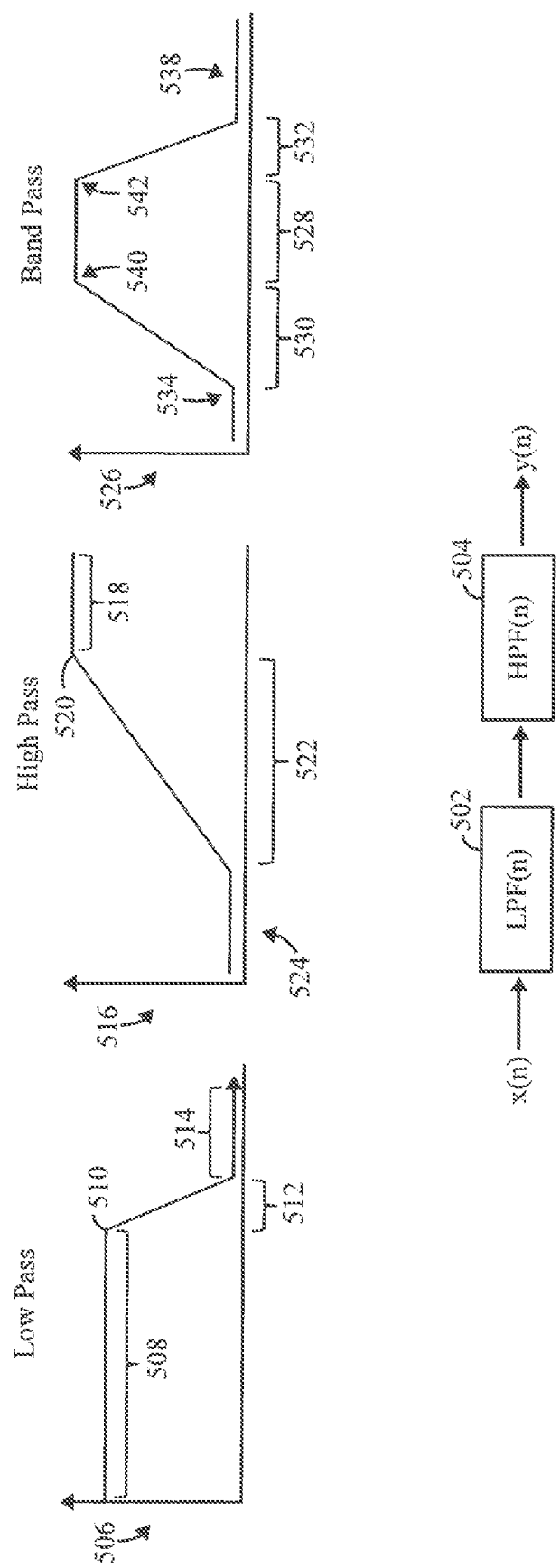
FIG. 5 illustrates a block diagram of an example hybrid filter circuit that may be obtained by interconnecting a select combination of first and higher order filter circuits in a cascaded manner in accordance with embodiments herein.

FIG. 5 illustrates a block diagram of an example hybrid filter circuit that may be obtained by interconnecting a select combination of first and higher order filter circuits in a cascaded manner. In FIG. 5, an input signal X (n) is provided to a low-pass filter circuit 502. The low-pass filter circuit 502 having a frequency response that is defined based on a transfer function LPF (n). Graph 506 illustrates an example for the transfer function LPF (n), having a passband 508 up to a cutoff frequency 510. A transition region 512 follows the cutoff frequency 510 until reaching a stopband 514. The frequency response exhibits an attenuation that increases at a predetermined rate that exhibits a relatively close tolerance and a relatively fast/steep slope along the transition region 512. By way of example, the low-pass filter 502 may be implemented by a higher order filter circuit (e.g., 306 in FIG. 3) and/or a cascade combination of higher order filter circuits. It may be desirable to utilize a higher order filter circuit to define the frequency response of the low-pass filter 502 when the attenuation characteristic of interest exhibits relatively close tolerances, such as a relatively fast/steep slope that cannot be defined by a first order filter circuit.

The output of the low-pass filter circuit 502 is supplied as an input to a high-pass filter circuit 504 having a frequency response that is defined based on a transfer function HPF (n). Graph 516 illustrates an example for the transfer function HPF (n), having a passband 518 after a lower cutoff frequency 520. A transition region 522 precedes the cutoff frequency 520, with a stopband 524 preceding the transition region 522. The frequency response exhibits an attenuation that increases at an attenuation rate that exhibits a relatively wide tolerance and a relatively slow/flat slope along the transition region 522. The attenuation rate within the transition region 522 associated with the high-pass filter 504 is lower/slower than the attenuation rate within the transition region 512 associated with the low-pass filter 502. By way of example, the high-pass filter 504 may be implemented by a first order filter circuit (e.g., 304 in FIG. 3) and/or a cascade combination of first order filter circuits. It may be desirable to utilize a first order filter circuit to define the frequency response of the high-pass filter 504 when the attenuation characteristic of interest exhibits relatively wide tolerances, such as a relatively slow slope that can be defined by one or more first order filter circuits.

The output Y(n) of the high-pass filter circuit 504 has a composite frequency response corresponding to a bandpass filter. Graph 526 illustrates an example for the transfer function Y (n) having a passband 528 between a lower transition region 530 and an upper transition region 532. The lower transition region 530 is preceded by a stopband 534, while the upper transition region 532 is followed by a stopband 538. The passband 528 is bordered by lower and upper cutoff frequencies 540 and 542. The attenuation within the lower transition region 530 has an attenuation rate defined by (e.g., substantially similar to) the attenuation rate within the transition region 522 of the high-pass filter in graph 516. The attenuation within the upper transition region 532 has an attenuation rate defined by (e.g., substantially similar to) the attenuation rate within the transition region 512 of the low-pass filter in graph 506. It is recognized that the shape of attenuation within the transition regions 530 and 532 of the composite frequency response may vary from the shape of attenuation within transition regions 512 and 522, due in part to the convolution of the low-pass and high-pass filters 502, 504. Additionally or alternatively, while the present example illustrates the frequency response for each of the segments within the graphs 506, 516 526 to be relatively linear, it is recognized that the frequency response in each of the corresponding segments may follow alternative nonlinear shapes.

The foregoing example describes a switch matrix (e.g., 308 in FIG. 3) that interconnects first and higher order filter circuits in a cascading manner. Additionally or alternatively, the switch matrix may interconnect first and higher order filter circuits by subtraction and/or addition of the output signals from the corresponding first and higher order filter circuits with one another. The low-pass filter 502 may be formed by one or more first order filter circuits, while the high-pass filter 604 may be formed by one or more high order filter circuits. Additionally or alternatively, one or more of the high and low pass filter circuits 502, 504 may be formed by a combination of first and higher order filter circuits.

Figure 6:
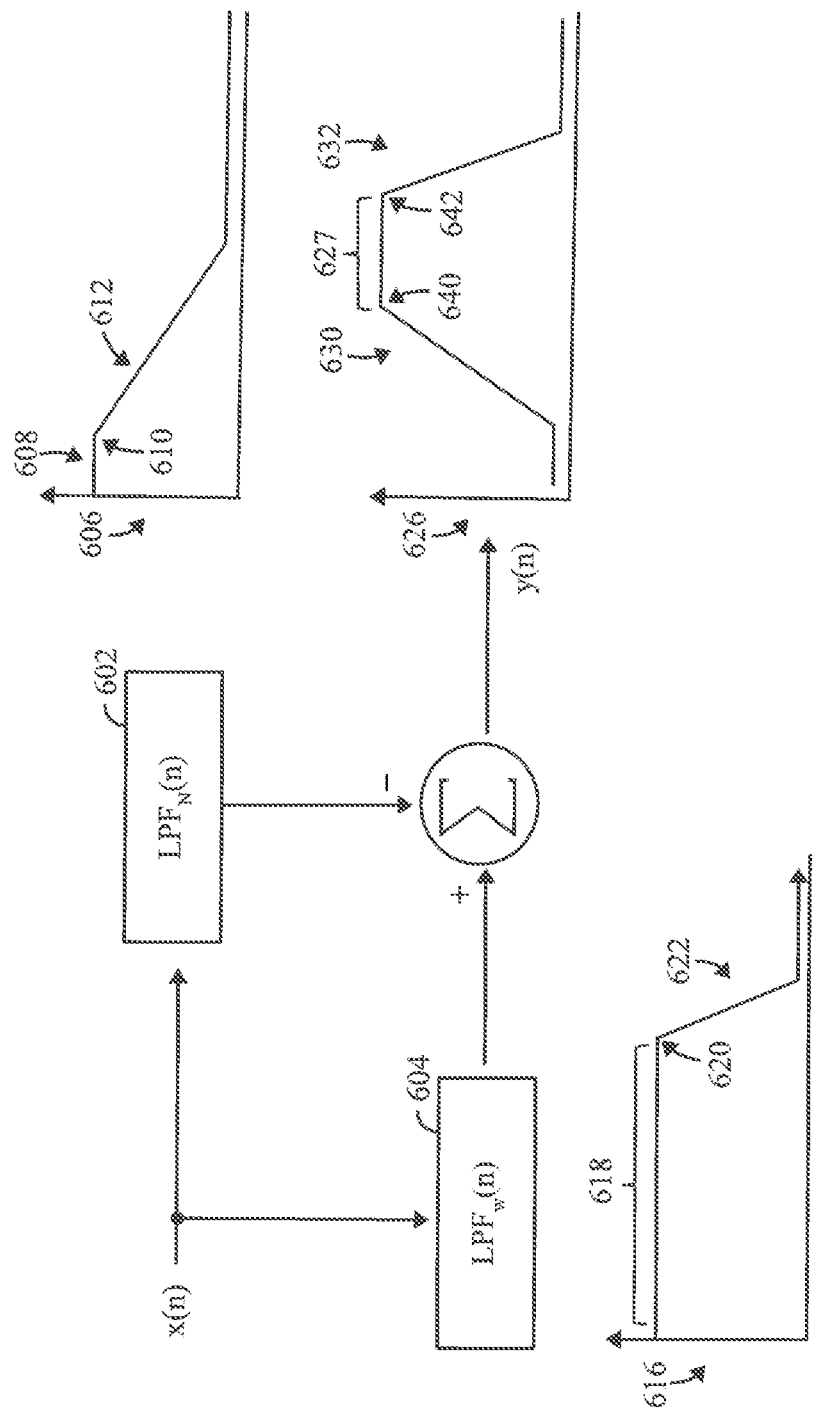
FIG. 6 illustrates a block diagram of an example hybrid filter circuit that may be obtained by interconnecting a select combination of first and higher order filter circuits through subtraction and/or addition of the output signals there between in accordance with embodiments herein.

FIG. 6 illustrates a block diagram of an example hybrid filter circuit that may be obtained by interconnecting a select combination of first and higher order filter circuits through subtraction and/or addition of the output signals there between. In FIG. 6, an input signal X (n) is provided in parallel to a narrow band low-pass filter circuit 602 and a wide band low-pass filter circuit 604. The narrow band low-pass filter circuit 602 has a frequency response that is defined based on a transfer function $LPF_N(n)$, while the wide band low-pass filter circuit 604 has a frequency response that is defined based on a transfer function $LPF_w(n)$.

Graph 606 illustrates an example for the transfer function $LPF_N(n)$, while graph 616 illustrates an example for the transfer function $LPF_w(n)$. Graph 606 has a narrow passband 608 relative to a wide passband 618 for graph 616. The graph 606 has a frequency response over a transition region 612 that exhibits a first attenuation characteristic (e.g., a first relatively slow rate), as compared to a second attenuation characteristic of a frequency response over a transition region 622 in graph 616. The second attenuation characteristic over the transition region 622 has a second relatively fast attenuation rate.

The output signal from the narrow band low-pass filter 602 is subtracted from the output signal for the wide band low-pass filter 604 to form an output signal having a composite frequency response of interest as illustrated by graph 626. The graph 626 exhibits a passband at 628 that is preceded and followed by lower and upper transition regions 630, 632. The passband 627 has cutoff frequencies 640 and 642 that generally correspond to the cutoff frequencies 610, 620 of the graphs 606, 616. The composite frequency response of graph 626 exhibits an attenuation characteristic in the upper and lower transition regions 630, 632 that substantially corresponds to the attenuation characteristics within the transition region 612, 622, respectively, for the narrow and wide band low-pass filters 602, 604.

The narrow band low-pass filter 602 may be formed by one or more first order filter circuits, while the wide band low-pass filter 604 may be formed by one or more higher order filter circuits. Additionally or alternatively, one or more of the narrow and wide band low-pass filter circuits 602, 604 may be formed by a combination of first and higher order filter circuits.

In accordance with embodiments herein, the HSP circuit affords various advantages over conventional systems. As one example, at least some embodiments of the HSP circuit do not sacrifice performance by limiting the HSP circuit 300 to one particular class/order of filter circuits. For example, using only one class of filters (e.g., biquad filters) may provide a desired filter performance, but may exceed a filter power factor. Conversely using only first order integer filters may provide a desired filter power factor, but would restrict the frequency response programmability. Depending on the overall desired filter characteristics (e.g., frequency response and power factors), embodiments herein provide a hybrid mixture of high resolution filters, low resolution filters, lower power filters and high-power filters. The high resolution-high-power filters provide fine grain filtering to achieve desired pass bands, while the low resolution-low power filters provide coarse grain stop band filtering at a very low power cost.

In accordance with embodiments herein, the HSP circuit supports multiple implementation choices for choosing power and performance from a particular network thus reducing the need for costly changes in integrated circuits that are formed with only one class of filters therein.

Figure 7:
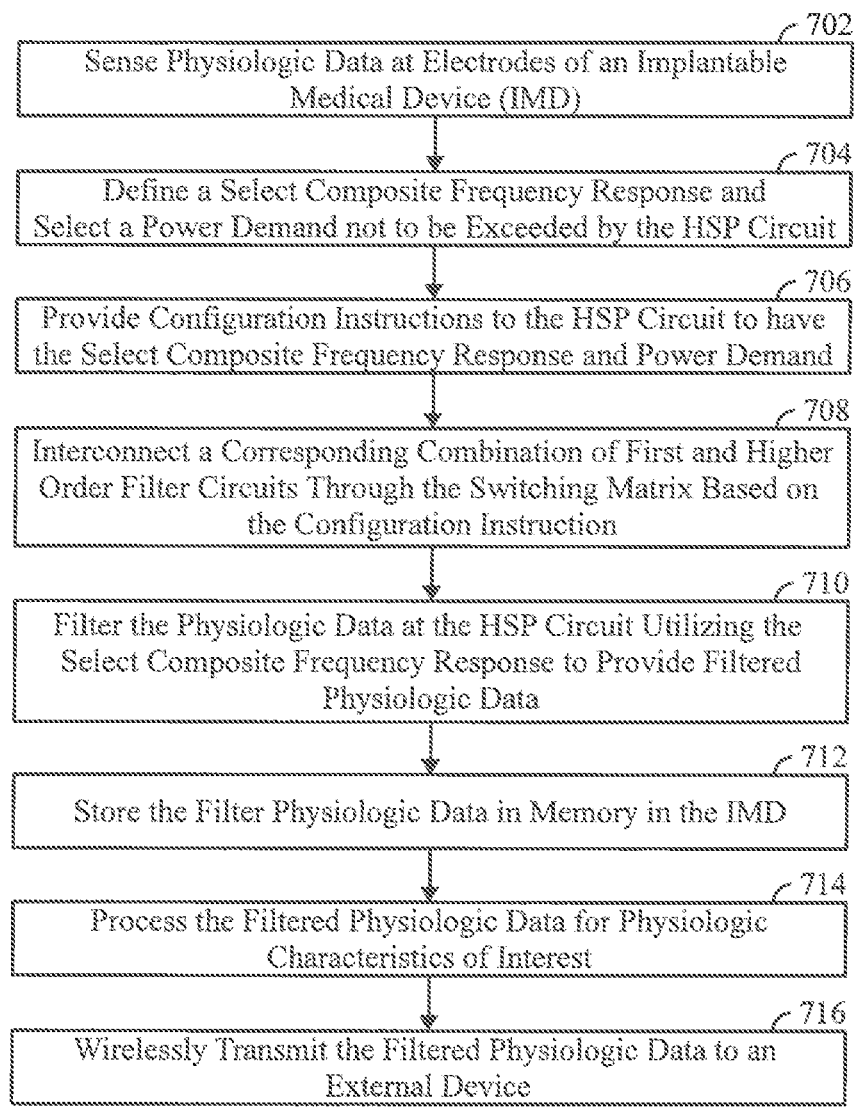
FIG. 7 illustrates a flowchart for processing sensed signals in accordance with embodiments herein.

FIG. 7 illustrates a flowchart for processing sensed signals in accordance with embodiments herein. At 702, physiologic data is sensed at electrodes of an implantable medical device and a sensing circuit as described above. At 702, the physiologic data is directed to a HSP circuit, such as HSP circuit 120, to perform signal processing operations. Additionally or alternatively, the physiologic data can be received from memory unit 94, the microcontroller 60, telemetry circuit or otherwise.

At 704, the method defines a select composite frequency response and a select power demand that should not be exceeded by the HSP circuit. The select composite frequency response and/or power demand may be automatically or manually determined. For example, the defining operation may comprise programming integer filters utilizing integer coefficients to define the plurality of first order filters in the HSP circuit.

Additionally or alternatively, the defining operation may comprise providing second order recursive digital filters as the plurality of higher order filters in the HSP circuit. Additionally or alternatively, the defining operation may configure bi-quadratic digital filters as the higher order filters, the biquadratic digital filters having different corresponding frequency passbands or cutoff frequencies. Additionally or alternatively, the defining operation may comprise configuring the plurality of first order filters as low-pass integer filters with different corresponding low-pass frequency ranges and as high-pass integer filters with different corresponding high-pass frequency ranges; and interconnecting at least a portion of the low-pass integer filters, high-pass integer filters and bi-quadratic filters in a cascaded manner to form the hybrid filter having the select composite frequency response. Optionally, the defining operation may comprise configuring the plurality of first order filters as low-pass integer filters with different corresponding low-pass frequency ranges and as high-pass integer filters with different corresponding high-pass frequency ranges; and interconnecting at least a portion of the low-pass integer filters, high-pass integer filters and bi-quadratic filters in an additive or subtractive manner to form the hybrid filter having the select composite frequency response. Optionally, the defining operation may comprise defining the select composite frequency response based on a convolution of a frequency response of at least one of the plurality of first order filters and a frequency response of at least one of the plurality of higher order filters. Optionally, the defining operation may comprise configuring at least one of the higher order filters as a wideband low-pass filter and configuring at least one of the first order filters as a narrowband low-pass filter, the narrowband low-pass filter having a cutoff frequency below a cutoff frequency of the wideband low-pass filter. Optionally, the defining operation may comprise configuring at least one of the higher order filters to have a frequency response exhibiting a first attenuation rate in a corresponding transition region and configuring at least one of the first order filters to have a frequency response exhibiting a second attenuation rate in a corresponding transition region, the first attenuation rate being greater than the second attenuation rate.

At 706, one or more processors as described herein provide configuration instructions to a hybrid signal processing (HSP) circuit to have the select composite frequency response and to utilize no more than a select power demand. For example, the HSP circuit may be configured based on configuration instructions from the microcontroller 60. Additionally or alternatively, the HSP circuit may be configured based on remote configuration instructions received wirelessly at the telemetry circuit 100 from an external device 102. For example, the remote configuration instructions may be determined by a physician or other administrative person and wirelessly transmitted to the IMD.

At 706, the HSP circuit reconfigures the interconnected combination of first and higher order filter circuits based on the configuration instructions received. The ages P circuit interconnects a combination of one or more first order filters from a plurality of first order filters and one or more higher order filters from a plurality of higher order filters.

At 710, the HSP circuit filters the physiologic data utilizing the select composite frequency response to provide filtered physiologic data. At 712, the IMD stores the filtered physiologic data in memory in the IMD. At 714, the IMD processes the filtered physiologic data for physiologic characteristics of interest. At 716, the telemetry circuit wirelessly transmits the filtered physiologic data to an external device.

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

The units/modules/applications herein may include any processor-based or microprocessor-based system including systems using microcontrollers reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carded out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other, in addition, many modifications may be made to adapt a particular situation or material to the teachings herein without departing from its scope. While the dimensions, types of materials and coatings described herein are intended to define various parameters, they are by no means limiting and are illustrative hi nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method of processing data in an implantable medical device (IMD) comprising:
utilizing a hybrid signal processing (HSP) circuit having a select composite frequency response that utilizes no more than a select power demand, the HSP circuit defining the select composite frequency response by interconnecting a combination of one or more first order filters from a plurality of first order filters and one or more higher order filters from a plurality of higher order filters;
sensing physiologic data at a sensing circuit, the physiologic data indicative of a physiologic characteristic of a patient;
filtering the physiologic data at the HSP circuit utilizing the select composite frequency response to provide filtered physiologic data; and
configuring at least one of the higher order filters as a wideband low-pass filter and configuring at least one of the first order filters as a narrowband low-pass filter, the narrowband low-pass filter having a cutoff frequency below a cutoff frequency of the wideband low-pass filter.

2. The method of claim 1, further comprising at least one of processing or storing the filtered physiologic data.

3. The method of claim 1, further comprising programming integer filters utilizing integer coefficients to define the plurality of first order filters in the HSP circuit.

4. The method of claim 1, further comprising providing second order recursive digital filters as the plurality of higher order filters in the HSP circuit.

5. The method of claim 1, further comprising configuring bi-quadratic digital filters as the higher order filters, the biquadratic digital filters having different corresponding frequency passbands or cutoff frequencies.

6. The method of claim 5, further comprising configuring the plurality of first order filters as low-pass integer filters with different corresponding low-pass frequency ranges and as high-pass integer filters with different corresponding high-pass frequency ranges; and interconnecting at least a portion of the low-pass integer filters, high-pass integer filters and bi-quadratic filters in a cascaded manner to form the hybrid filter having the select composite frequency response.

7. The method of claim 5, further comprising configuring the plurality of first order filters as low-pass integer filters with different corresponding low-pass frequency ranges and as high-pass integer filters with different corresponding high-pass frequency ranges; and interconnecting at least a portion of the low-pass integer filters, high-pass integer filters and bi-quadratic filters in an additive or subtractive manner to form the hybrid filter having the select composite frequency response.

8. A method of processing data in an implantable medical device (IMD), comprising
utilizing a hybrid signal processing (HSP) circuit having a select composite frequency response that utilizes no more than a select power demand, the HSP circuit defining the select composite frequency response by interconnecting a combination of one or more first order filters from a plurality of first order filters and one or more higher order filters from a plurality of higher order filters;
sensing physiologic data at a sensing circuit, the physiologic data indicative of a physiologic characteristic of a patient;
filtering the physiologic data at the HSP circuit utilizing the select composite frequency response to provide filtered physiologic data; and
defining the select composite frequency response based on a convolution of a frequency response of at least one of the plurality of first order filters and a frequency response of at least one of the plurality of higher order filters.

9. The method of claim 8, further comprising at least one of processing or storing the filtered physiologic data.

10. The method of claim 8, further comprising programming integer filters utilizing integer coefficients to define the plurality of first order filters in the HSP circuit.

11. The method of claim 8, further comprising configuring bi-quadratic digital filters as the higher order filters, the biquadratic digital filters having different corresponding frequency passbands or cutoff frequencies.

12. A method of processing data in an implantable medical device (IMD), further comprising
utilizing a hybrid signal processing (HSP) circuit having a select composite frequency response that utilizes no more than a select power demand, the HSP circuit defining the select composite frequency response by interconnecting a combination of one or more first order filters from a plurality of first order filters and one or more higher order filters from a plurality of higher order filters;
sensing physiologic data at a sensing circuit, the physiologic data indicative of a physiologic characteristic of a patient;
filtering the physiologic data at the HSP circuit utilizing the select composite frequency response to provide filtered physiologic data; and
configuring at least one of the higher order filters to have a frequency response exhibiting a first attenuation rate in a corresponding transition region and configuring at least one of the first order filters to have a frequency response exhibiting a second attenuation rate in a corresponding transition region, the first attenuation rate being greater than the second attenuation rate.

13. The method of claim 12, further comprising at least one of processing or storing the filtered physiologic data.

14. The method of claim 12, further comprising programming integer filters utilizing integer coefficients to define the plurality of first order filters in the HSP circuit.

15. The method of claim 12, further comprising providing second order recursive digital filters as the plurality of higher order filters in the HSP circuit.

16. The method of claim 12, further comprising configuring bi-quadratic digital filters as the higher order filters, the biquadratic digital filters having different corresponding frequency passbands or cutoff frequencies.

17. The method of claim 16, further comprising configuring the plurality of first order filters as low-pass integer filters with different corresponding low-pass frequency ranges and as high-pass integer filters with different corresponding high-pass frequency ranges; and interconnecting at least a portion of the low-pass integer filters, high-pass integer filters and bi-quadratic filters in a cascaded manner to form the hybrid filter having the select composite frequency response.

18. The method of claim 16, further comprising configuring the plurality of first order filters as low-pass integer filters with different corresponding low-pass frequency ranges and as high-pass integer filters with different corresponding high-pass frequency ranges; and interconnecting at least a portion of the low-pass integer filters, high-pass integer filters and bi-quadratic filters in an additive or subtractive manner to form the hybrid filter having the select composite frequency response.

19. The method of claim 12, further comprising defining the select composite frequency response based on a convolution of a frequency response of at least one of the plurality of first order filters and a frequency response of at least one of the plurality of higher order filters.

20. The method of claim 12, wherein configuring at least one of the higher order filters further includes forming at least one of the higher order filters as a wideband low-pass filter and configuring at least one of the first order filters as a narrowband low-pass filter, the narrowband low-pass filter having a cutoff frequency below a cutoff frequency of the wideband low-pass filter.

\* \* \* \* \*